United States Patent [19]
Grammont

[11] Patent Number: 5,944,757
[45] Date of Patent: Aug. 31, 1999

[54] TOTAL TROCHITERO-ACROMIAL SHOULDER PROSTHESIS

[75] Inventor: Paul Marie Grammont, Dijon, France

[73] Assignee: Medinov-Amp, France

[21] Appl. No.: 08/836,629

[22] PCT Filed: Sep. 23, 1996

[86] PCT No.: PCT/FR96/01483

§ 371 Date: May 1, 1997

§ 102(e) Date: May 1, 1997

[87] PCT Pub. No.: WO97/10779

PCT Pub. Date: Mar. 27, 1997

[30] Foreign Application Priority Data

Sep. 22, 1995 [FR] France .................................. 95 11 169

[51] Int. Cl.[6] .................................................... A61F 2/40
[52] U.S. Cl. ............................................................. 623/19
[58] Field of Search .................................... 623/16, 18, 19

[56] References Cited

U.S. PATENT DOCUMENTS

| D. 285,969 | 9/1986 | Kinnett | 623/19 |
|---|---|---|---|
| 3,979,778 | 9/1976 | Stroot . | |
| 4,550,450 | 11/1985 | Kinnett | 623/18 |
| 4,990,161 | 2/1991 | Kampner | 623/16 |
| 5,032,132 | 7/1991 | Matsen, III et al. | 623/19 |
| 5,080,673 | 1/1992 | Burkhead et al. | 623/19 |
| 5,593,448 | 1/1997 | Dong | 623/19 |

FOREIGN PATENT DOCUMENTS 2541890  9/1984  France .

*Primary Examiner*—David H. Willse
*Attorney, Agent, or Firm*—Bierman, Muserlian and Lucas

[57] ABSTRACT

Total trochitero-acromial shoulder prosthesis comprising two elements, namely, a trochiterian element (13), having the shape of a convex spherical sector, and equipped with means for fastening to the site of the trochiter, and an acromial element (12) having a bearing surface for the trochiterian element (13) and equipped with means for fastening to the lower face of the acromion, in such a way as to cover the afore-mentioned trochiterian element, and whose dimensions are such that the acromional element remains free to move, without overshooting the clavicle, as one with the acromion, once the latter has been sectioned at the level of the pillar of the scapular spine and a method of using the same.

14 Claims, 2 Drawing Sheets

TOTAL TROCHITERO-ACROMIAL SHOULDER PROSTHESIS

The present invention relates to a total trochitero-acromial shoulder prosthesis, that is to say a prosthesis which is intended to treat the mechanical and rheumatic disorders of the shoulder, which are known in particular under the term ruptures of the cuff, or scapulo-humeral periarthritis.

It is recognized that these disorders are excessively frequent and that they lead to an unnatural articulation between, on the one hand, the arch formed by the acromion and the acromio-coracoid ligament, and, on the other hand, the trochiter and the muscles which have their insertion there and which are then gradually destroyed.

This false articulation is painful and leads to premature restriction of the movement of the humerus in relation to the scapula.

The present invention aims to restore this freedom of movement of the shoulder and to eliminate the pain due to the aforementioned disorders, it being understood that the mechanical articulation of the shoulder, that is to say the gleno-humeral articulation, is unaffected.

The patent FR-A-2 418 644 has already proposed a prosthesis comprising two elements, namely: a trochiterian element having the shape of a spherical sector equipped with means for fastening to the site of the trochiter which has been sectioned beforehand, and an acromio-coracoid element having substantially the shape of a cylindrical or spherical segment intended to constitute an artificial articular arch by fastening, via one of its ends, to the coracoid apophysis, and via its other end to the lower face of the acromion, in such a way as to cover the aforementioned trochiterian element, its axis passing through the centre of the gleno-humeral articulation.

Total shoulder prostheses have also already been proposed, such as those described in the patent U.S. Pat. No. 4,550,450, in which a trochiterian prosthesis cooperates with a glenoid prosthesis and an acromial prosthesis placed under the end part of the acromion, and whose main length extends transversely towards the resectioned end of the clavicle. Such a prosthesis affords a function substantially identical to that described in the aforementioned French patent or in the patent FR-A-2 541 890, in which a single acromio-glenoid prosthesis serves as a seat for the trochiterian ball.

In order to move the humeral head downwards during abduction of the humerus in the glenoid cavity of the scapula, it has already been proposed that the trochiterian element in the shape of a spherical sector be off-centred laterally with respect to the centre of the humeral head or the glenoid cavity, in such a way as to bear under the acromio-coracoid element during abduction of the humerus by acting as a cam and effecting a concomitant lowering of the head of the humerus during the abduction.

However, in a number of cases, and particularly in cases of absence or total inefficiency of the periarticular or capsular muscles, which normally effect an active downward movement of the humeral head in the event of abduction or elevation of the arm, the prosthesis, and consequently the bone tissues supporting it, may be subjected to very high stresses, which may be damaging in the long term.

The present invention proposes to solve this problem in the case where the pulley effect of the elevator muscle heads of the deltoid muscle is, in view of the aforementioned stresses, insufficient to effect a suitable lowering of the humeral head during contraction of the deltoid muscle.

The prosthesis according to the invention comprises two elements, namely: a trochiterian element, for example of the type described in the patent FR-A-2 418 644, having the shape of a convex spherical sector whose diameter is preferably equal to or less than that of the humeral head, and equipped with means for fastening to the site of the trochiter, and an acromial element having a bearing surface for the trochiterian element and equipped with means for fastening to the lower face of the acromion, in such a way as to cover the aforementioned trochiterian element, and whose dimensions are such that it remains free to move, without overshooting the clavicle, as one with the acromion, once the latter has been sectioned at the level of the pillar of the scapular spine.

Thus, once the acromion has been sectioned at the level of this pillar, but remaining fixed to the clavicle and to the top of the trapezius muscle by way of intact tendons and ligaments, the assembly constituted by the acromion and the acromial prosthesis element forms a true patelliform element which, upon deltoid contraction, bears strongly on the humeral head so as to lower it. This pulley effect is all the greater as the elevation of the arm commences. It is annulled when clavicle, acromion and humerus are situated in the same horizontal plane at the end of elevation.

The bearing surface of the acromial element can advantageously be concave, it being possible for the radius of concavity, preferably spherical, to be greater than or substantially equal to the radius of the convex spherical sector of the trochiterian element, for the purpose of reducing or eliminating transverse movements of the two elements in relation to one another.

The size of the acromial element can be such that it occupies substantially the whole length of the acromion released by resection at the level of the pillar of the scapular spine.

It is generally preferable for the acromial prosthesis element not to overshoot the lower face of the part of the acromion which has been released from the scapular spine by sectioning at the level of the pillar.

The invention also relates to a method for implanting this prosthesis, which includes, in addition to the step of implanting the trochiterian element in a manner already known, the sectioning of the acromion at the level of the pillar of the scapular spine and the fastening of the acromial prosthesis element under the acromion, either before or after sectioning, the acromion, with its acromial prosthesis element, then remaining free in relation to the scapular spine so as to act as a patelliform articulation.

As in the case of French patent ER-A-2 418 644, the trochiterian element can be off-centred laterally with respect to the centre of the humeral head.

The trochiterian element can advantageously consist of a spherical segment, preferably metallic, comprising one or more anchoring pins which can be fastened by cement, or by any other means known per se, in holes which are formed in the trochiterian part of the humeral head, shaped by sectioning or machining, as is described in the aforementioned French patent.

According to a first embodiment of the invention, the trochiterian element consists of a solid spherical segment equipped with an anchoring pin which can be fastened, by cement or by any other means known per se, in a shaft which is formed in the sectioned trochiterian part of the head of the humerus.

In this case, the trochiterian element can be made of high-density polyethylene or any other similar material.

In one variant of the invention, the trochiterian element has the shape of a spherical cap whose edge has a plurality of fastening tabs which are intended to be anchored and fastened, by cement or by any other suitable means, in shafts which are formed to receive them in the sectioned trochiterian part of the head of the humerus.

In this case, the trochiterian element can be made either of high-density polyethylene or of metal, such as stainless steel of a quality tolerated by the human body, polished or covered with a high-density ceramic such as, for example, chromium oxides or any other material exhibiting great hardness and capable of being polished and honed in order to give perfect sliding.

The inner face of the trochiterian element can advantageously be covered with roughened areas or with an open-pore ceramic in order to perfect the bonding of the face to the sealing cement which is being used, such as methyl methacrylate.

The presence of an open-pore ceramic additionally allows bone to retake.

The acromial element consists of one piece, preferably made of high-density polyethylene, and preferably covering the whole of the lower face of the acromion. Its articular surface is a concave sphere and has substantially the same diameter as the convex spherical trochiterian part. The bonding face of this acromial element is designed to match the lower face of the acromion, which is slightly concave, and to present fastening means such as studs or pegs which can be securely fastened in holes which are formed on the lower face of the acromion.

The acromial element can also be made of a metal having sufficient mechanical strength to act as a patelliform arch for the trochiterian element. This acromial element is then advantageously made of polished stainless steel of a quality tolerated by the human body.

This material is perfect when the trochiterian element is made of polyethylene or of a metal covered with a high-density ceramic; but it will be evident that, conversely, it would also be possible to have a trochiterian element having the shape of a spherical cap made of polished stainless steel, with at least the lower face of the acromial element being covered with a high-density ceramic.

That surface of the acromial element intended to come into contact with the lower face of the acromion can advantageously be treated in such a way as to afford a degree of surface roughness facilitating the retake of bone, or else can be covered with different means facilitating this retake, such as, for example, a layer of hydroxyapatite or an open-pore ceramic, for example alumina.

Different fastening means which are known can of course be used, and in particular cements. However, the use of hydroxyapatite is often desirable in order to complement the mechanical fastening means, whatever these might be, whose operational effects are immediate. In fact, on top of the primary fastening ensured by these mechanical means, the hydroxyapatite sprayed over a surface which is intended to be in contact with an osseous face ensures a secondary fastening in the first few months following the surgical intervention; this fastening, which is complementary to the mechanical fastening, is of a physicochemical nature and is obtained by adsorption of the bone constituents onto the hydroxy-apatite; this is generally calcium hydroxyapatite.

Other advantages and characteristics of the invention will become clear from reading the following description which is given by way of non-limiting example and in which reference is made to the attached drawing, in which.

Figure 1:
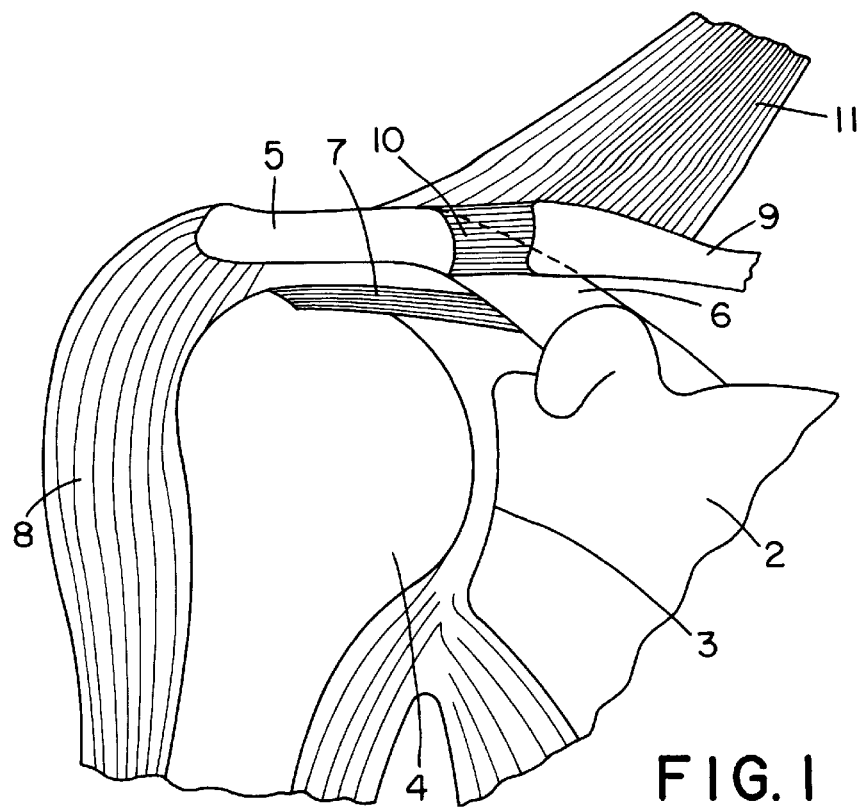
FIG. 1 is a diagrammatic frontal cross-section of a shoulder in a normal state.

FIG. 1 shows the scapula 2 with its glenoid cavity 3 cooperating with the articular surface of the humeral head 4. The latter is surmounted by the acromion 5 joined to the scapula via its pillar 6. The humeral head is separated from the acromion by the insertion of the supraspinous muscle 7. The deltoid muscle 8, attached to the external part of the clavicle, the acromion and the scapular spine, thus surrounds the humeral head. The acromion 5 is also attached to the clavicle 9 via the acromio-clavicular ligaments 10, and the trapezius muscle top 11 is common to the acromion and to the clavicle.

Figure 2:
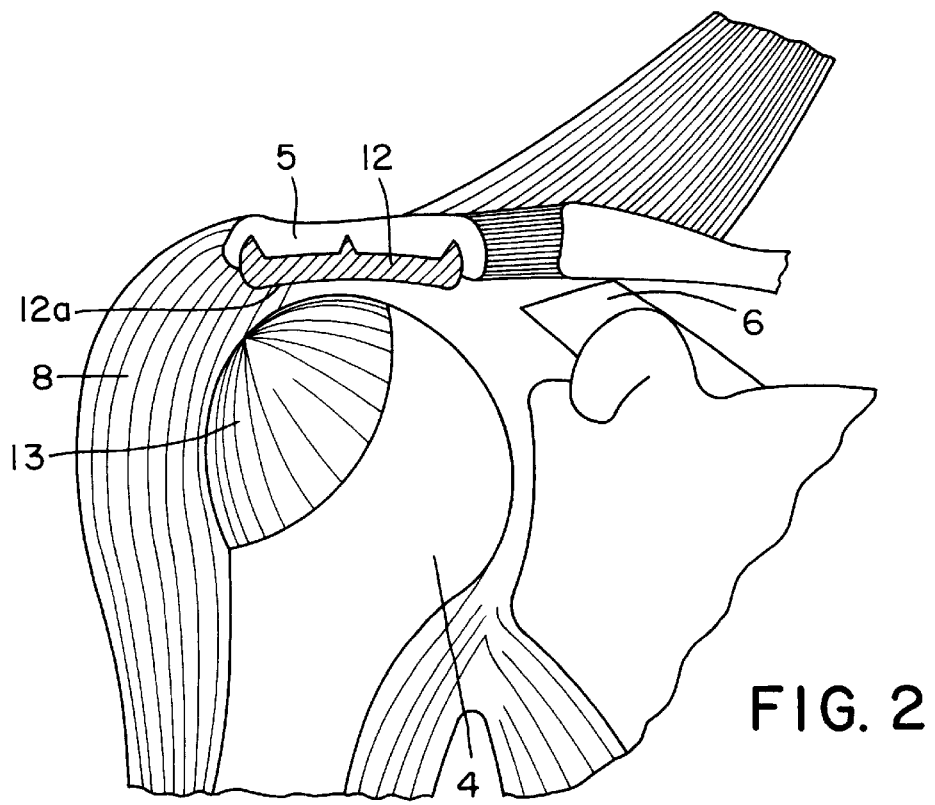
FIG. 2 is a frontal cross-section of a shoulder including the prosthesis, at the start of elevation of the arm.

Referring to FIG. 2, this shows a shoulder provided with a prosthesis according to the invention. The acromion 5 has been separated by sectioning of its pillar 6, and the supraspinous muscle 7 has disappeared because of the disorder.

The acromial prosthesis element 12 has a concave spherical articular surface 12a and, as can be seen in the drawing, it does not overshoot the clavicle, and therefore does not interfere with the coracoid apophysis. It is held fixed in the acromion, and on the lower face thereof, by studs penetrating into shafts which the surgeon forms in the acromion, in which it is sealed using a conventional surgical cement.

The trochiter has been removed and replaced by the trochiterian prosthesis element 13 in the shape of a spherical cap having substantially the same radius as that of the concave cap 12a.

The thickness of the acromial element 12 is preferably of the order of 8 to 10 mm, in such a way as to compensate for the empty space left below the acromion by the disappearance of the supraspinous muscle. The thickness is increased in order to heighten the power of the movement.

The muscular tension of the muscles of the humeral cuff can be controlled by the choice of the thickness of the acromial prosthesis or by the choice of the position or length of the trochiterian element along the humeral diaphysis.

It is possible, for example, to provide a set of several acromial elements 12 of different length and/or thickness.

Figure 3:
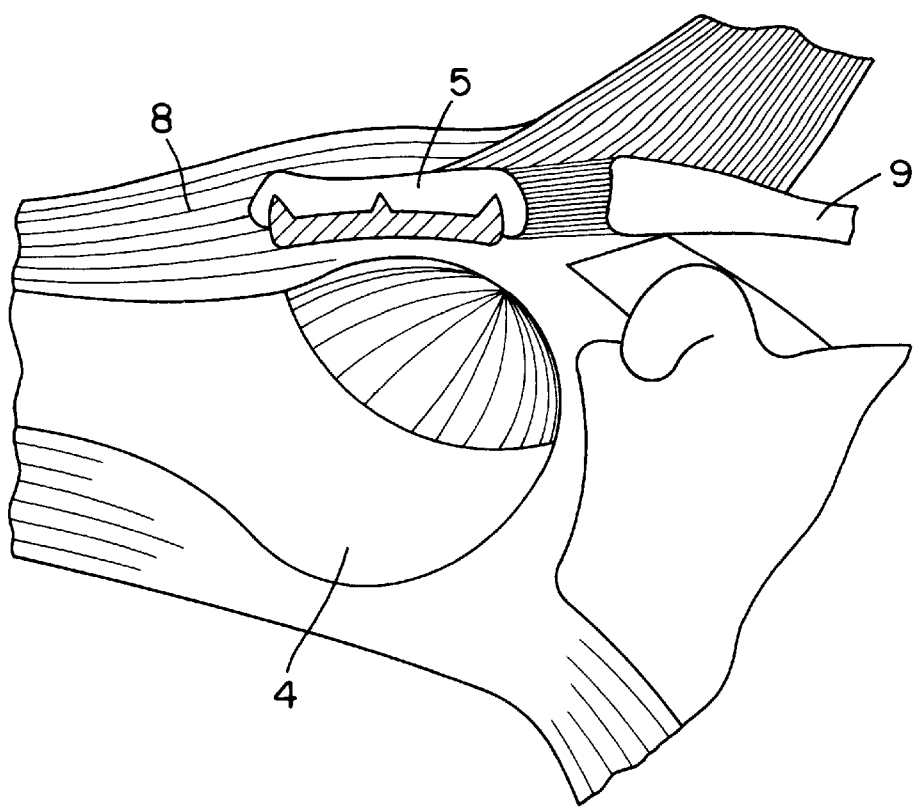
FIG. 3 is a frontal cross-section of a shoulder including the prosthesis, at the end of the elevation movement.
Figure 4:
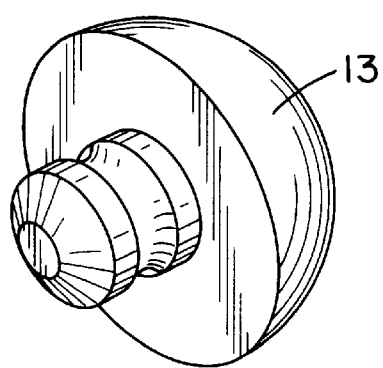
FIG. 4 is a perspective view of the trochiterian prosthesis element.
Figure 5:
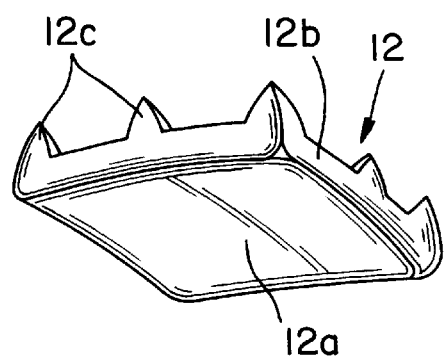
FIG. 5 is a perspective view of the acromial prosthesis element.

In the position in FIG. 2, at the start of elevation of the arm, the acromion 5, with its prosthesis 12, is drawn downwards by the contraction of the deltoid muscle 8. The sub-acromial prosthesis part 12 then comes to bear downwards on the humeral head by way of the trochiterian element 13. It will be appreciated that the pressure of the acromion on the humeral head will decrease as the arm is raised, and it will be seen from FIG. 3 that when the humerus 4 is horizontal, the deltoid muscle 8, the patelliform assembly formed by the acromion 5 and the acromial prosthesis element 12, and the clavicle 9 are practically aligned in a horizontal plane.

For fastening it under the lower face of the acromion 5, separated from its pillar, the upper face 12b of the acromial element 12 can be equipped with pegs or studs 12c intended to penetrate into recesses hollowed out in the acromion and to be cemented therein. The abovementioned upper face 12b, along with the studs 12c, is advantageously treated either by surface treatment or by covering with a layer of an appropriate material in order to facilitate its osseous integration.

I claim:

1. Method for implanting a total trochitero-acromial shoulder prosthesis comprising a trochiterian element having the shape of a convex spherical sector and equipped with means for fastening to the site of the trochiter, and an acromial element (12) having a bearing surface for the trochiterian element (13) and equipped with means for fastening to the lower face of the acromion, the acromial element being configured to cover the trochiterian element and being dimensioned to remain free to move, without overshooting the clavicle, as one with the acromion, the latter having been sectioned at the level of the pillar of the scapular spine, the method comprising implanting the trochiterian element, sectioning the acromion at the level of the pillar of the scapular spine, and fastening the acromial prosthesis element under the acromion, such that the prosthesis remains free in relation to the scapular spine so as to act as a patelliform articulation.

2. The method of claim 1 wherein the acromial prosthesis element (12) does not overshoot the lower face of the part of the acromion which has been released from the scapular spine by sectioning at the level of the pillar.

3. Method according to claim 1, wherein the tension of the muscles of the rotator cuff of the shoulder is controlled by acting on the thickness of the acromial element.

4. Total trochitero-acromial shoulder prosthesis comprising: a trochiterian element (13) having the shape of a convex spherical sector and equipped with means for fastening to the site of the trochiter, and an acromial element (12) having a bearing surface for the trochiterian element (13) and equipped with means for fastening to the lower face of the acromion, the acromial element being configured to cover the trochiterian element and being dimensioned to remain free to move, without overshooting the clavicle, as one with the acromion, the latter having been sectioned at the level of the pillar of the scapular spine.

5. Prosthesis according to claim 4, wherein the said bearing surface is concave.

6. Prosthesis according to claim 4, wherein the said bearing surface has a radius substantially equal to that of the sector of the trochiterian element.

7. Prosthesis according to claim 4, wherein the acromial element (12) dimensioned to cover the whole of the lower face of the released part of the acromion.

8. Prosthesis according to claim 4, wherein an upper face (12*b*) of the acromial element (12) is designed to match the lower face of the acromion and the fastening means (12*c*) is adapted to be fastened in holes formed in the lower face of the acromion.

9. Prosthesis according to claim 4, wherein the thickness of the acromial element is of the order of 8 to 10 mm.

10. Prosthesis according to claim 4, wherein the fastening means of the trochiterian element (13) comprises one or more anchoring pins.

11. Prosthesis according to claim 4, wherein the trochiterian element is made in the form of a spherical cap.

12. Prosthesis according to claim 4, wherein the trochiterian element and/or the acromial element is made of metal, or of high-density polyethylene.

13. Prosthesis according to claim 12, wherein a bonding face of the trochiterian element (13) and/or of the acromial element (12) is treated or covered with a material facilitating bonding to a sealing cement and osseous integration.

14. Prosthesis according to claim 4, wherein a bonding face of the trochiterian element (13) and/or of the acromial element (12) is covered with hydroxyapatite.

* * * * *

UNITED STATES PATENT AND TRADEMARK OFFICE
CERTIFICATE OF CORRECTION

PATENT NO. : 5,944,757
DATED : August 31, 1999
INVENTOR(S) : Paul Marie Grammont It is certified that error appears in the above-identified patent and that said Letters Patent is hereby corrected as shown below:

Title page, item [73], Assignee, change "Medinov-Amp. France" to --
Medinov-Amp. France and Paul Marie Grammont, France--

Signed and Sealed this

Twenty-fourth Day of October, 2000

Attest:

Q. TODD DICKINSON

*Attesting Officer*  *Director of Patents and Trademarks*